(12) United States Patent
Whiteley et al.

(10) Patent No.: US 8,012,461 B2
(45) Date of Patent: Sep. 6, 2011

(54) BIOFILM REMOVER

(75) Inventors: Reginald Keith Whiteley, North Manly (AU); Marilyn Emily Karaman, Waratah West (AU)

(73) Assignee: Wireley Corporation Pty Ltd, North Sydney (AU)

( * ) Notice: Subject to any disclaimer, the term of this patent is extended or adjusted under 35 U.S.C. 154(b) by 842 days.

(21) Appl. No.: 11/629,052

(22) PCT Filed: Jun. 1, 2005

(86) PCT No.: PCT/AU2005/000782
§ 371 (c)(1),
(2), (4) Date: Feb. 19, 2007

(87) PCT Pub. No.: WO2005/120592
PCT Pub. Date: Dec. 22, 2005

(65) Prior Publication Data
US 2008/0317877 A1    Dec. 25, 2008

(30) Foreign Application Priority Data

Jun. 8, 2004 (AU) ................................ 2004903116

(51) Int. Cl.
*A61L 9/00* (2006.01)
*C11D 1/62* (2006.01)
(52) U.S. Cl. ........................................ 424/70.28; 422/28
(58) Field of Classification Search ................ 422/28; 424/70.28
See application file for complete search history.

(56) References Cited

U.S. PATENT DOCUMENTS

| | | | | |
|---|---|---|---|---|
| 4,978,685 A | * | 12/1990 | Gannon et al. | 514/642 |
| 2003/0161758 A1 | * | 8/2003 | Whiteley | 422/28 |

* cited by examiner

*Primary Examiner* — Sean E Conley
(74) *Attorney, Agent, or Firm* — Pryor Cashman LLP; Andrew S. Langsam, Esq.

(57) ABSTRACT

A composition for the removal of biofilms from substrate surfaces formed by reacting: (a) one or more quaternary halide surfactants with (b) a source of reactive bromine ions in the ratio of 1 halide ion forming part of the quaternary surfactant to 0.05 to 8 moles of bromine ions in aqueous solution.

15 Claims, No Drawings

BIOFILM REMOVER

TECHNICAL FIELD

The present invention relates to formulations and methods useful in the removal of surgical soils and in sterilizing used surgical appliances and ancillary fibre optic and electronic accessories intended for immediate reuse without damage to chemically sensitive components.

ART

Total removal of contaminants from surgical instruments, and particularly the internal surfaces of structurally intricate fibre optic surgical instruments, more commonly known as endoscopes, under practical conditions, is proving considerably more difficult than previously believed. This is primarily because of the existence of bacterial biofilm underlying other types of soiling matter.

Currently contaminants are removed from surgical instruments by first pre-cleaning with detergents containing various enzymes and then exposing the instruments to sterilizing chemical disinfectants. This may occur by either manual means or by use of integrated washer-disinfectors (WDs), the latter being used wherever possible for the sake of consistency and quality of result.

The most common method for cleaning surgical instruments used at this time, world wide, comprises the following steps:
1. The instruments are dismantled by hand.
2. The external surfaces of the instrument parts are cleaned by hand using approved brushes and an "Instrument Detergent" (ID), that commonly contains one or more chemical enzymes to help dissolve and remove surgical soils within and on the external surfaces deposited during surgery. Following this the instrument parts are cleaned in a WD using an approved cycle.
3. The instrument parts are rinsed with water and blow dried with air.
4. Following this the instrument parts are either immersed in or have high level disinfectants or chemical sterilants circulated therethrough. These disinfectants/sterilants are commonly either 2 percent glutaraldehyde or 0.5 percent peracetic acid. This step may be conducted at room temperature or under heat up to a maximum of 45° C.
5. Finally the instrument parts are rinsed with sterile water and stored under appropriate conditions.

When these procedures are performed meticulously the processed instruments are generally considered to have achieved the accepted standard of cleaning and disinfection. However, despite the best of care in performing these procedures, a small number of future surgical operations using instruments cleaned by these procedures are followed by quite serious post-operative bacterial and/or viral infections. Examples are infection with the AIDS virus (HIV), Hepatitis B & C and the SARS virus, the infectious microbe(s) being carried forward from patient to patient within incompletely removed biofilm.

Probable causes of these instances of post-operative infection have been the subject of intensive research at the University of Sydney, Australia, Department of Infectious Diseases. This has shown that post-operative infection from endoscopes is possible even when the best available reprocessing procedures are used by skilled personnel. A probable cause of post-operative infection was found to be the previously undetected existence of serious biofilms within processed instruments containing viable common surgical pathogens.

Extensive research showed that presently recommended methods of reprocessing endoscopes failed to remove biofilms thus allowing pathogens to be transferred between patients. This finding revealed the urgent need to develop improved processing procedures, and especially chemical cleaning products that would remove biofilms deposited in endoscopes following surgery.

The research further showed that biofilms that formed on surgical grade Teflon and polyvinylchloride plastic surfaces possess properties not previously reported. Two particular aspects of these finding were determined as strategically important to the reprocessing of used endoscopes.

The formation of biofilm has been found to occur in distinct phases visually identifiable by electron microscopy. Initially a first layer of interlocking bacterial cells join longitudinally and adhere to the surface of a substrate to form a film/lattice-like formation across the surface. This is tenaciously bound to the substrate by a unique polysaccharide based adhesive. The composition of this layer differs significantly depending on the bacterial systems, the substrates and the culture media. This layer serves as a tenacious base layer for the subsequent deposition of more complex extracellular polysaccharide (EPS) deposits and will be referred to herein as the "basal layer".

Once the basal layer is sufficiently formed (i.e. perhaps only several cells deep) a softer biolayer is progressively deposited throughout and above this layer. This biolayer is normally composed of polysaccharide, glycoprotein and contains varying amounts of lipoprotein and is referred to as extracellular polysaccharide (EPS). The EPS deposit continues to form until equilibrium is established in a particular ecosystem, whereby loose surface EPS sloughs into surrounding aqueous medium and is replaced by newly formed EPS.

It has been found that basal layer remaining after traditional cleaning may contain vegetative bacteria and blood borne virus. It has also been found that subsequent treatment with high level disinfectants (HLD) and chemical sterilants do not kill all of the pathogens remaining in the basal layer (*Battling Biofilms* J W Costerton & P S Stewart, Scientific American, July 2001, pages 60-75).

Thus two critical findings have emerged. Firstly, where biofilms remain within the channels of endoscopes, sterility of endoscopes can not be guaranteed. Secondly, existing methods of cleaning used endoscopes do not totally remove biofilm from endoscopes.

When cleaning and disinfecting surgical instruments it is desirable that the chemicals used are not hazardous to humans. This is particularly desirable in many smaller health facilities where the cleaning and sterilizing of surgical instruments may be carried out by hand, often in confined areas adjacent to surgical suites. It is also necessary that these chemicals can be rinsed free to ensure no foreign chemical is left on instrument surfaces after cleaning. Residues of chemicals accidentally left on or within hollow endoscopic tubing must not present any form of post-operative sequela such as chemical irritation or damage to open tissue surrounding or adjacent to an operation site.

The use of enzyme containing detergents introduces potential human occupational health and safety concerns for staff engaged in cleaning endoscopes. Enzymes used in detergent formulations are a major potential respiratory sensitiser. The use of fully automated cleaning equipment to clean and disinfect dissembled endoscopes under sealed conditions should adequately control exposure to enzymatic cleaning products. However, sprays or aerosols may be emitted when endoscope washers are opened after reprocessing cycles, or when the seals of endoscope washers wear allowing fume leakage while the washers are in operation. Great care must be taken during manual cleaning in order to reduce the risk of inhalation of aerosols (or dusts caused by the drying out of detergent residues). Such inhalation may result in sensitisation, or even more serious health issues (*Extrinsic allergic alveolitis from a proteolytic enzyme* A Tripathi & L C Grammer, Ann Allergy Asthma Immunol 2001, 86, 425-427).

Several recent patents have addressed the problem of removal of obdurate basal biofilm in very small channels in endoscopes. U.S. Pat. No. 6,475,434 uses derivatives of N-acetylcysteine to deposit film on cleaned instruments, usually as part of a deposited coating to prevent adhesion of biofilm to surgical surfaces. While the method appears effective as designed, the use of the active ingredient N-acetylcysteine alone or in combination with detergent systems fails to penetrate and dislodge strongly adherent basal biofilm. This is presumed to be because of its inability to penetrate through biofilm to react with and release the primary adherent polysaccharide adhesive binding the film to the surface of the substrate, during cleaning and subsequent rinsing.

DESCRIPTION OF THE INVENTION

We have found that the fibrous structure that is produced as part of the basal structure of biofilms is much less reactive to detergents, oxidising agents, acids, enzyme containing detergent and alkali than EPS and other soiling components found routinely in biofilms on used endoscopes. Total removal of all of the biofilm requires total breakage of the forces of adhesion that bind the basal structure to the surface of the substrate.

Patent application WO 02/07789 A1 discloses a composition to remove biofilm. It employs a combination of strongly cationic compounds in conjunction with specific surfactants, special solvents and chelating agents and is presently preferred as the best method for cleaning used endoscopic instruments. The cleaning action of this latter type of formulation differs from previous methods of removing biofilm from surgical equipment. The older methods used enzyme based detergents and relied upon the compositions reacting with and dispersing glutinous EPS as a first step to releasing the basal adhesive layer. In contrast the WO 02/07789 A1 formulations successfully penetrate the basal layer of the biofilm and release the film virtually intact leaving a clean surface containing far fewer retained infective organisms.

Extensive field testing with products of WO 02/07789 A1 has shown that in a limited number of surgical procedures there remains the possibility that small patches of still adherent basal biofilm may be found in very difficult to reach areas within very small channels of endoscopes. Further research has demonstrated the need to provide improved compositions to remove aged and largely concealed biofilm deposits. This work concentrated upon discovering chemicals and/or combinations of chemicals that would provide the following two additional mechanisms:

(a) better penetration into and dislodgement of biomass, and
(b) production of specific reactivity to the biomass of biofilms; in particular towards the strongly adhesive underlying basal layer.

A new reaction mechanism has been identified that occurs between surfactants of a specific group (technically described as surfactants capable of forming a strong positive quaternary charge on their hydrophilic group) and the ionic form of oxidising biocides, in particular those of the halogen type. Binding occurs between the positively charged hydrophile of the surfactant and ions of the oxidising agent, possibly with the formation of shielded interhalogen structures. The formation of interhalide type compounds is described in "Inorganic Chemistry" $2^{nd}$ edition Schriver D F et al., 5 pp 552-559 Oxford Press (1994). The ionic complexes formed from this new reaction represent a new class of biocidal surfactants that possess very strong oxidising properties.

These new quaternary surfactants have been found to be particularly effective in removing biofilms and their components from surfaces of substrates. Equally important is the synergistically increased biocidal potency, due, we believe, to the increase in oxidising potential of the species, which is increased many fold above that exhibited by the basic quaternary surfactant. The effective biocidal spectrum of the new quaternary surfactant complex is also increased in particular against more chemically resistant microbes such as mycobacteria, bacterial spores, fungi and algae.

These new surfactants demonstrate more rapid and more complete dispersion of EPS to effectively expose the basal layer to penetration and release by the surfactant complex, which is aided by supplementary detersive ingredients.

The new surfactants may be used alone or in formulations that include other special solvents and detergent auxiliaries known to have positive effects upon biocide components. For example they may be used with other compatible surfactants and common detergent adjuncts to promote wide detergent activity against the large range of organic soils that are encountered on used surgical instruments.

Likewise, these surfactants may be used in combination with water conditioning agents including common non-corrosive chelating agents, organic and inorganic acidic and alkaline buffer salts to regulate the pH of ready-to-use solutions of biofilm detergents and some small molecule water soluble organic compounds to further contribute to the overall effectiveness of the compositions.

The surfactants that can be used in the new reaction mechanism are quaternary halide surfactants and include:

a) mono and di-quaternary ammonium halide surfactants the hydrophile of which may be of ionised chlorine or iodine;
b) the mono and di substituted phosphonium halides, in particular chlorides, of which decyl tributyl phosphonium chloride is a common commercial example;
c) members of the group of hydroxy alkyl (C4-16) phosphonium halides;
d) members of the Gemini group of multi-quaternary and zwitterion surfactants (Rist O. et al *Molecules* 2001: 6, 979-987;
e) and hydroxy quaternary ammonium halides and other BOLARFORM group surfactants (Davey T W et al Aust J. Chem 1998: 51 581-585).

Any suitable ionic forms of oxidising biocides may be used in the new reaction mechanism identified by the inventors. Preferably these biocides comprise inorganic or organic sources of bromine ions. Sources of bromine ions suitable for the purposes of this invention may be derived from water saturated with bromine gas. They may also be derived from water containing organic nitrogen compounds which allow up to 15% bromine to be dissolved in stable form. Organic nitrogen containing compounds that allow dissociation of free bromine ions in aqueous solutions include for example 1-bromo-3-chloro-5,5-dimethyldantoin and bromosulfamic acid and its ammonium salt.

Useful adjuncts that may be included in compositions containing the new surfactants include small molecule compounds that can reduce the viscosity of proteinaceous material within biofilms by attacking the bonds to medical substrates.

Biofilm biomass is known to contain mucin which has strongly adhesive properties. To remove the mucin it is desirable to include in the composition of the invention agents (i.e. mucolytes) having specific reactivity to double sulphide bonds that are critical to the viscosity of mucoidal structures at pHs in the range 7-11 in aqueous solution. Examples of these agents include bromohexine (2 amino 3,5 dibromobenzyl cyclohexyl methylamine), glycerol guaicolate (3'-(2-methoxyphenoxy)propane 1,2 diol), N-acetyl cysteine, carbocysteine, dithioreitol, tris(2-carboxyethyl) phosphine and methyl cysteine and alkyl (C6-14) thioethyl ether amines. Of these bromohexine is the more chemically stable in aqueous solution and most effective. These mucolytes are preferably pre-dissolved in a small amount of hydrotropic solvent in combination with one of the surfactants forming part of this invention.

Also of benefit as a co-solvent to assist penetration of polysaccharides in biomass are some alkyl phosphate esters such as tributyl phosphate and tributoxy ethyl phosphate small amounts of which can be incorporated into suitable formulations by pre-dissolving in low molecular weight water soluble organic constituents. These ingredients also contribute usefully to interfacial wetting of the soil masses in question.

Experiments using these latter groups of chemicals demonstrated quicker removal of hard biofilm masses including the normally unreactive essentially polysaccharide basal layer from both medical grade teflon and polyvinyl chloride substrates.

It was found that the addition of selected low molecular weight nitrogen containing solvents facilitate complete removal more particularly of proteinaceous constituents of biofilms leaving clean, essentially sterile surfaces on test substrates.

According to a first aspect of the invention there is provided a composition for the removal of biofilms from substrate surfaces formed by reacting:

(a) one or more quaternary halide surfactants with
(b) a source of reactive bromine ions in the ratio of 1 halide ion forming part of the quaternary surfactant to 0.05 to 7 moles of bromine ions in aqueous solution.

Preferably the halide is a chloride or iodide ion.

The composition may additionally comprise one or more non-ionic or zwitterion surfactants.

The composition may additionally comprise one or more phosphate esters or ethers dissolved in water, or mixtures of water and polar solvent selected from the group consisting of C(1-7) alcohols, ethers, esters and ketones.

The composition may additionally comprise one or more ingredients selected from the group consisting of detergent additives, hydrotropes, inorganic and organic buffering agents, sequestering and chelating agents, viscosity control additives, dyes and perfumes compatible with the other ingredients.

The present invention also provides an aqueous medical residue treatment composition which comprises:

(a) a quaternary halide surfactant,
(b) a solution containing ionised bromine to react with the halide ion of the surfactant; and
(c) one or more non-ionic or zwitterion containing surfactants, having a pH in the range 4 to 12 in aqueous solution.

Typically the halide is chloride or iodide.

Preferably, the aqueous medical residue treatment composition additionally comprises:

a) one or more phosphate esters: and/or
b) one or more polar solvents partly or wholly soluble in water.

Optionally one or more other common ingredients of commercial detergents may be present including those selected from the group consisting of hydrotropes, inorganic and or organic buffering agents, sequestering or chelating agents, viscosity control additives, dyes and perfumes.

The present invention also provides a biofilm and medical residue removal treatment product which includes:

a) from 1 part per million to 250,000 parts per million of one or more alkyl or alkyl aryl (C8-18) mono or di quaternary halide surfactants having either a chlorine or iodine negatively charged ion in the quaternary group
b) an aqueous solution or other source of reactive bromine containing from 0.1 to 200,000 parts per million of reactive bromine ions
c) one or more non-ionic or zwitterion containing surfactants comprising a hydrophobe containing 7 to 20 carbon atoms
d) a mucolytic agent
e) a phosphate ester or ether
f) a low molecular weight nitrogen containing solvent having a molecular weight of less than 120
g) one or more polar alcohol, glycol, ester, ether or ketone solvents having a molecular weight of less than 200, in a solution having a pH of from 4 to 12 which may optionally contain one or more hydrotropic agents, inorganic or organic buffering agents, and other common acidic and alkaline detergent additives.

The present invention further provides a composition of the invention formulated as a dilutable concentrated product or as a diluted ready to use product provided in the form of:

a) a single package containing all ingredients;
b) two or more packages containing one or more of the ingredients of the formulation.

In particular a single package may be provided comprising a surfactant and a source of bromine. Alternatively these ingredients may be provided in two separate packages. Additional ingredients may be provided in these packages or in one or more further packages.

The inventors have surprisingly found that compositions of this nature provide a simple easy-to-use, non-corrosive, safe, near neutral chemical detergent that efficiently and reliably cleans endoscopes and other used surgical equipment. In exceptional cases, alkaline salts confer added reactivity to the formulated products.

Whilst not wishing to be bound by theory, the present inventors believe that non-ionic or zwitterion surfactants exhibit very effective penetrating action into the bulk exopolysaccharide (EPS) glutinous mass in biofilms as well as binding blood proteins that normally comprise the bulk of medical soils. Preferably 0.05 to 8.0 mole of ionic bromine is added to 1 mole of ionic chlorine or iodine to form an oxidative hydrophile group. It is thought that this oxidative hydrophile group amplifies both the penetration of the hydrophobe and causes chemical change to the adhesive biofilm components to secure the quick and complete removal of all biofilm.

The non-ionic or zwitterion surfactant is chosen by study of the effect of micellar behavior upon the reactivity of brominated surfactants that fall within the scope of this invention.

Moreover the oxidative effect of the interhalogen complex of the hydrophile greatly increases reactivity of the total surfactant molecule to micro-organisms, in particular to more chemical resistant species such as bacterial spores, mycobacteria, fungi, algae, and more resistant viruses such as hepatitis group, polio group and SARS.

The mucolytic agent, when present, contributes to the removal of the biofilm process by facilitating penetration into the proteinaceous components of EPS. It is thought that the mucolytic agent reduces the viscosity of the EPS by reacting with or otherwise loosening disulphide bonds that are responsible for viscosity, thereby allowing more rapid and complete penetration throughout the biofilm and the basal layer. It is also believed to usefully assist in attacking the basal adhesive layer by facilitating rehydration of the adhesive proteins involved thus reducing the adhesive force between the bacterial cells in the basal layer and the substrate allowing total biofilm removal.

The low molecular weight nitrogen containing solvents which are preferably employed have the distinct ability within this system to assist in rehydrating and dispersing basal adhesive protein and providing specific solubilizing action towards rehydrated and degenerated proteins. Other organic matter associated with the biofilm may be removed by the detergent and dispersive action of complimentary surfactants and detergent additives.

These ingredients together serve in a synergistic manner, each complementing the properties of the other in the multi-step process of removing biofilm from medical substrates. The action of this combination is assisted in clearly defined ways by use of a compatible surfactant to provide useful wetting action by lowering air-water surface tension in aqueous solution below a preferred 28 dyne/centimeter. Likewise a simple buffer system maintains operating pH at the optimum for maximum performance of the products of this invention.

Similarly the use of a small quantity of an efficient chelating agent serves usefully to counteract the affect of hard water where used in endoscope reprocessing procedures with these preparations as well as to release divalent metal bonds commonly found as binding components in biological films and gels.

Hydrotropic type chemicals also contribute to the overall performance of the final products herein envisaged. This is believed to be due to their ability to assist in rehydrating condensed (denatured) proteins. They also contribute to chemical stability of the concentrated aqueous solutions of the invention.

Whilst not being bound by theory it is thought that the compositions of the invention remove biofilm by distinctly different mechanisms than normal detergents containing enzymes. Normal detergents, including those containing enzymes, clean by the processes of penetration and dispersion. In contrast it is hypothesised that the compositions of this invention work by attacking or penetrating and dislodging the primary adhesive layer binding the basal layer to the substrate.

The initial binding of basal film is due to a layer of strongly adsorbed hydrated tightly coiled protein secreted from the cell walls of bacteria. Surface adsorption of this protein is, by many workers, believed to be the first step in creation of a boundary layer between a substrate and bacterial cells. Subsequent excretions of polysaccharide EPS by bacteria provides adhesion of whole cells to a substrate and the formation of mature biofilms. Some alkaline detergent salts have been demonstrated to assist in uncoiling complex protein structures thereby assisting interaction with previously shielded reactive groups.

The exact composition of this primary adhesive layer may vary considerably according to the species of microorganism, the composition of the environment in which the biofilm develops and the chemical nature of the substrate, the latter being shown to regulate which genes a microbe activates to secure initial adhesion. The initial reactions driving the deposition of the initial protein layer are believed to involve a combination of hydrophobic reactions and electrostatic interactions between the cell wall of the bacterium and the substrate. Tests conducted by the present inventors pointed strongly to destruction or weakening of bonds within the primary adhesive layer as the key to efficient removal of total biofilm from the substrates involved in endoscope construction.

We therefore set out to determine chemical mechanisms that could be successfully applied to break the forces of adhesion involved between the surface of Teflon and PVC.

Biofilms of the representative bacteria *Escherishia coli* and *Pseudomonas aeruginosa* were grown over a six (6) day period from standard cultures at room temperature within Teflon and PVC tubing supplied by manufacturers as equivalent to that employed in medicine and surgery. These were then washed with sterile water, sectioned and subjected to exposure to test detergents under controlled representative flow conditions for 5 or 10 minutes. They were then washed in sterile water and prepared for SEM examination and subjected to determination of both viable and dead bacterial cells by well accepted and documented laboratory techniques.

After screening a wide range of chemicals theoretically capable of contributing to removal of the basic adhesive layer it was determined that additional groups of chemicals could prove useful in a cleaning formulation include:

1. The group of organic phosphates consisting structurally of alkyl (C6-16) tributyl phosphonates demonstrated unusual ability to penetrate and disperse the softer EPS that comprised the majority of bacterial biofilms. The action of this group of organic phosphates and similar phosphonates equals if not exceeds the action of multi-component enzyme containing detergents for pre-cleaning used endoscopes. However, alone these chemicals will neither remove basal biofilm nor render surfaces free of vegetative micro-organisms. Phosphonate chelating agents such as 1,2,5 tricarboxybutane-phosphate may, under some practical conditions, compliment or assist the reaction of this cationic species with biofilm components.
2. When the remnants of biofilm are viewed by SEM the remaining basal matrix comprises firmly attached cells and partly disintegrated matter, presumably more condensed polysaccharide polymer EPS. Mucolytic agents and low molecular weight organic nitrogen containing solvents and compounds with appropriate dimensional shapes and electronic configuration in aqueous solution assist in solvating adhesive protein or at least alter its surface chemistry to allow interaction with other detergent ingredients.
3. Specialised surfactants are able to wet and thereby surface attach to biofilm components thereby hastening removal of softer EPS thus permitting better access to the underlying adhesive layer and penetration of the hydration sheaf surrounding the adhesive proteinaceous matter.
4. Some protonic solvents have also been shown to assist in solvating and/or displacing the hydration sheaf of the adhesive protein layer by reducing its viscosity by processes not readily identifiable.

The use of an adequate quantity of an appropriate chelating agent substantially increases the opportunity of a detergent to release a soil associated with biofilm from medical surfaces where either hard water salts are found or where di and/or trivalent ions are part of adhesive processes within biofilms.

Similarly the alkali metal salts of some low molecular weight organic acids employed as buffer salts have been shown to assist in release of biofilms, in particular lithium and sodium salts. Used in combination in the appropriate quantity at a pH from 5.0 to 10.0 these enhance the removal of biofilms, presumably through helping to solvate denuded protein residues promoting micellar interactions, to facilitate surfactant penetration of the condensed chemically resistant polysaccharide layer of which the shell of the basal layer of bacterial biofilms is believed to comprise.

The effectiveness of the alkali metal counterion in assisting penetration of the EPS follows the series lithium>sodium>potassium. In the preferred embodiment of the invention the lithium ion has been shown to be superior as a cation in both reactivity to biofilm components as well as assisting in reducing the number of viable microbes associated with medical biofilms. This is believed due to the unique property of the lithium ion to react with organic surfaces in much the same manner as the hydrogen ion, forming reactive hydrogen type bonds as well as ionic and covalent bonds under appropriate aqueous conditions.

In a preferred embodiment a suitable chelating agent may be any stable organic compound capable of forming stable complexes with divalent, trivalent and transition metals, such as, but not limited to, derivatives of ethylenediamine tetraacetic acid, tetrahydroxy ethylenediamine, propylenediamine tetraacetic acid, ethylenediamine disuccinic acid, oxalates, pyrophates, nitrilotriacetic acid, dihydroxyglycine, aminopoly phosphonates, and phosphonobutane 1,2,4-tricarboxylic acid.

The organic acids useful as buffer salts in the invention may be carboxylic acids or derivatised carboxylic acids. Examples of low molecular weight organic acids that form useful reactive salts with monovalent metals are C 1-8 carboxylic acids and hydroxyorganic acids including but not limited to formates, acetates, lactates, tartrates, citrates, propionates, hydroxyacetates, acetoacetates, acrylates, hydroxymethylacrylates methylacrylates, benzoates and salicylates. Derivatised carboxylic acids include phosphorylated and sulfhydrylated derivatives and bromosulfamic acid. Thioglycolic acid salts are also active in this regard.

Monovalent salts of simple inorganic acids can be used in conjunction with organic acids to suit specific circumstances, for example bicarbonates, carbonates, phosphates and silicates. These serve the beneficial purpose of both assisting in solubilizing softer EPS from biofilms as well as to further enhance the action of organic chelating agents and regulate the pH of working solutions of the products of this invention and contribute to micellar phenomenon.

The amount of organic chelating agent and monovalent organic salt to be included in the composition of the invention needs to be sufficient to optimize the detergent effect of the composition enhancing the ability of the composition to penetrate or remove biofilm.

In a preferred embodiment of the invention at least one organic chelating agent is present in an amount of from 0.05 to 5 percent by weight, preferably 0.5 to 3 percent, to assist in penetrating and solubilizing the basal constituent found in biofilms.

In the embodiments where the chelating agent is a lithium monovalent salt the amount of the compound added to the composition is sufficient to give a lithium concentration of between 50 and 15,000 parts per million. In a more preferred composition the concentration of lithium containing compound is sufficient to give a lithium ion concentration of between 250 and 2500 parts per million.

In a preferred embodiment the composition of the invention may include two or more surfactants that can be demonstrated to contribute usefully to the penetration and removal of biofilm components. Some of these surfactants as formulated may also exhibit useful biocidal properties to bacteria and some viruses as well as corrosion protection to metals. Biocidal activity of these surfactants is quite incidental and is not the primary aim in selection; rather their ability as surfactants to synergize with other components in the formulations of this invention to penetrate, dislodge, disperse and remove all traces of biofilms both EPS and basal material from medical surfaces and similar substrates is the basis for their selection.

Examples of surfactants useful in this invention are the C8-18 alkyl amine oxides, alkyl (C4-16) tributyl phosphonium halides and gluconates, commercial alkyl (C4-14) amphoteric and zwitterion surfactants, alkyl (C4-18) pyrrolidone derivatives, poloxamines, alkyl sulphosulphonates and cationic fluorocarbon and silane surfactants.

For the purposes of this invention, any surfactant that provides for a stable aqueous solution of key ingredients within the stabilized buffer pH conditions can be employed to achieve a pH at use dilution of 4 to 12 in this invention.

In a preferred embodiment, the compositions include at least one surfactant exhibiting an air-water surface tension of less than 28 dyne/centimeter which is present in an amount of from 0.025 to 20 percent by weight of a final composition. A more preferred embodiment of the invention includes at least one such surfactant in the amount of 0.1 to 30 percent, more preferably from 0.05 to 20 percent, and most preferably from 2.5 to 7.5 percent by weight in concentrated dilutable formulations.

Low molecular weight non-ionic surfactant having an alkyl chain of C5-16 and 4-12 mole of ethylene oxide attached are particularly useful, as are corresponding polypropylene derivatives and mixtures of polyethylene and polypropylene, so called block polymers. All surfactant must also be highly biodegradable. The selection of specific surfactants in the formulations of the invention is dependent on the specific components of the formulation, their interactions and contribution to the chemical stability of each particular formulation.

In a particularly preferred formulation an alkyl (C6-16) non-foaming polysaccharide surfactant is preferred, being compatible with all other preferred components involved in the most effective formulating biofilm remover.

Nitrogen containing compounds capable as acting as useful solvents in this invention include but are not limited to unreacted monoethanolamine, diethanolamine, triethanolamine and isopropylamine, acetamide and its C1-6 mono and dialkyl derivatives, the mono and dialkyl(C1-4) derivatives of methylamine, ethylamine and propylamine, alkyl (C1-4) amine oxides, guanidine and dimethyl guanidine and their halides, urea and thiourea (also including their mono and di alkyl derivatives) pyrrolidone, n-methyl pyrrolidone and the alkyl (C6-14) derivatives of pyrrolidone, glucosamine and its mono and dialkyl (C1-4) derivatives, sulphamic, chlorosulfamic and bromosulphanic acid and their ammonium salt and alkanolamides, and alkyl (C1-3) sulphamates and halogensulphonates.

In a preferred embodiment, the composition of this invention includes at least one surfactant present in an amount from 0.01 to 20 percent by weight, more preferably from 1 to 15 percent by weight.

Any safe to use organic polyhydric agent effective for penetrating and assisting in removal of biofilm components (possibly by a chaotropic type phenomenon), in particular glycoprotein and condensed polysaccharide residues in biofilms may be employed in the medical residue compositions of this invention. These may include at least one carrying solvent plus one or more low molecular weight highly polar substances that usefully assist in solubilising, penetrating and/or dispersing or dislodging the unique and chemically resistant polymeric polysaccharide adhesive layer binding basal biofilms to plastic medical surfaces.

In preferred embodiments, the composition of the invention includes at least one solvent selected from, but not limited to, one or more water soluble polar solvents chosen from alkyl and aryl primary and secondary alcohols, esters, ketones, aromatic alcohols, and nitrogen containing solvent with 8 or less carbon atoms, and glycols and polyols and their esters and ethers containing from 2 to 20 carbon atoms. In a particularly preferred embodiment, the composition of the invention includes at least one solvent selected from a glycol or alkanol, or a derivative thereof.

Any glycol or alkanol which is compatible with the other components of the composition may be included. Preferably the glycol or alcohol is a water soluble low molecular weight alkanol, glycol or a derivative thereof containing between 2 and 20 carbon atoms. More preferably the glycol is a polyethylene or polypropylene glycol derivative having from between 2 and 9 carbon atoms. Examples of suitable glycols are triethyleneglycol, dipropylene glycol and the mono and di methyl and ethyl ethers of ethylene and propylene glycol, especially propyleneglycol monomethyl ether.

In a preferred embodiment, the composition of the invention may include at least one solvent selected from but not limited to C1-8 alcohols, esters, ketones, ethers and glycols and their methyl and ethyl derivatives, aromatic alcohols containing 9 or less carbon atoms, phenol and benzyl alcohol.

In a preferred embodiment, the composition of the invention includes at least one solvent present in an amount from 0.5 to 25 percent, more preferably from 1.0 to 20 percent by weight.

In a preferred embodiment the composition contains low molecular weight amines, or amides or their mono or di alkyl (C1-10) derivatives. In a particularly preferred embodiment the composition includes at one co-solvent selected from but not limited to dibutyl acetamide, (thio)urea and dimethyl (thio)urea halides, guanidine halides, mono, di and triethanolamine, isopropanolamide, pyrrolidone, methylpyrrolidone, alkyl (C5-12) pyrrolidones and methyl thioglycollate.

In a preferred embodiment the composition of the present invention includes at least one co-solvent in an amount from 0.5 to 25 percent by weight and more preferably from 1 to 20 percent by weight.

In a further aspect the present invention provides a method of removal of a surgical soil and/or biofilm from a reusable surgical appliance, ancillary fibre optic or electronic accessory without damage to chemically sensitive components which method comprises treating the reusable surgical appliance, ancillary fibre optic, or electronic accessory with a composition of the first aspect of the invention.

In yet a further aspect the present invention provides the use of a composition of the first aspect of the invention in a method of the second aspect of the invention.

In a further aspect the present invention provides a reusable surgical appliance, ancillary fibre optic or electronic accessory treated by a method of the second aspect of the invention.

In a further aspect the present invention provides a process for the manufacture of a composition of the first aspect of the invention which method comprises combining the ingredients thereof in an aqueous solution having a pH at use dilution of 4 to 12.

In a further aspect the present invention provides a method for the removal of a surgical soil and/or biofilm from a reusable surgical appliance, ancillary fibre optic or electronic accessory without damage to chemically sensitive components which method comprises treating the reusable surgical appliance, ancillary fibre optic, or electronic accessory with a composition of the first aspect of the invention wherein the bromine ion may be incorporated with the quaternary surfactant either in a single product or by means of an additive added separately immediately before use.

In another aspect the present invention provides a process for the manufacture of a composition of the first aspect of the invention which method comprises combining the ingredients thereof to form a stable concentrated aqueous solution having a pH at use dilution of from 4 to 12.

The following examples illustrate some preferred embodiments of the invention. However, it should be understood that the following examples are illustrative only and should not be taken as a restriction on the generality of the invention as described above.

BEST METHOD AND OTHER METHODS OF CARRYING OUT THE INVENTION

Comparative Example 1

The present inventors conducted detailed research studies using the laboratory methods described in detail in WO 02/07789 A1 to compare three commonly used enzyme containing detergents with one neutral endoscope detergent and an experimental product derived from WO 02/07789 A1 referred to as EC5C as follows:

| | |
|---|---|
| Pure water | 69.8% by weight |
| Dodecylamine hydrobromide | 9.5 |
| Lauric diethanolamide, 95% active | 7 |
| Dipropyleneglycol | 6 |
| Dilithium ethylenediamine tetraacetate | 3.5 |
| Monoethanolamine | 2.5 |
| Citric acid | 1.7 |

This preparation was diluted 1 in 100 (1% v/v) in tap water at 20 or 35° C.

Each product was tested under identical conditions at both room temperature and 35° C. when dissolved in tap water at the concentration recommended on the product label.

Fresh biofilms were generated from *Escherishia coli* and *Pseudomonas aeruginosa*. Pre-prepared bacterial culture was circulated through the apparatus for 6 days to develop significant biofilms on internal tubing surfaces of either teflon or medical grade polyvinylchloride (PVC) tubing. These were then washed with sterile water and sectioned for subsequent testing either by surface examination by scanning electron microscope (SEM) or by bacterial examination to determine the numbers of viable and dead bacterial cells remaining after detergent exposure. Both were determined quantitatively.

This study established that EC5C was superior to both commercial enzyme containing and neutral instrument detergents in removing surgical soils and biofilm from endoscopic tubing but, even more importantly, gave a far greater reduction in numbers of virulent microbes remaining on internal surfaces after pre-cleaning. However, under these worst case conditions no one test piece was found to be totally free of biofilm.

Studies using scanning electron microscopes to examine cleaned surfaces revealed that isolated clumps of firmly bound biofilm could still be seen on both PVC and teflon surfaces after reprocessing, the amount remaining varying according to the efficacy of the detergent and the surface. Less remnant biofilm was observed consistently on PVC than on Teflon.

Very few clumps were found in the case of sample EC5C, representing more than 90 percent total removal of biofilm. The better of the enzyme containing detergents showed 70 percent removal while other products cleaned by less than 50 percent.

Importantly, the few clumps remaining after cleaning with EC5C appeared damaged by complete extraction of more reactive extracellular polymers substances (EPS) leaving a condensed structured deposit of the exo-skeleton of clumped bacterial cells. These were tenaciously bound to the underlying substrate.

It is only by total removal of biofilm from within endoscopes that a microbe free instrument can be assured after reprocessing.

The preceding experiments confirmed earlier findings that the EPS produced by microbes on a substrate are not uniform either in chemical composition, reactivity to detergents, or adhesion.

As a base control experiments described above with fresh biofilm of *E. coli* were conducted with a commercial nonionic instrument detergent and a series of enzyme containing instrument disinfectant presently sold internationally. After cleaning and rinsing the samples were examined for residual bacteria and viewed after staining but by optical and scanning electron microscope with the results Table 1.

TABLE 1

| Detergent | Initial culture cfu/mL | Recovered cfu/mL | Biofilm removal observations |
|---|---|---|---|
| Control | log 7.7 | log 7 | heavily soiled |
| Nonionic | 7.7 | 4.5 | lightly |
| Enzyme 1 | 7.7 | 4 | lightly |
| Enzyme 2 | 7.7 | 2.6 | lightly |
| Enzyme 3 | 7.7 | 3.4 | lightly |

While numbers of bacteria were reduced by cleaning with conventional detergents there remained a light film of EPS attached to the basal layer. This finding is consistent with that repeatedly reported in medical literature.

No product removed the complete biofilm. This testing was repeated with fresh biofilm produced by *Pseudomonas aeruginosa* with almost identical results.

The formulations of Examples 1 and 4, are anticipated to achieve total removal of biofilm as well as vegetative microbes within biofilms when employed under the preceding test conditions. The formulations of Examples 2 and 3 demonstrate the nature of formulations that achieve total removal of biofilm when employed under the preceding test conditions:

EXAMPLE 1

| | |
|---|---|
| Pure water | 80.0% w/w |
| Cetyl pyrimidium chloride | 7.5% w/w |
| Bromine water - 5.00% Br | 10.0% w/w |
| Alkyl (C8-14) polysaccharide | 2.5% w/w |

EXAMPLE 2

| | |
|---|---|
| Pure water | 67.75% w/w |
| Cetyl pyrimidium chloride | 7.5% w/w |
| Bromine water - 5% Br | 12.5% w/w |
| Bromohexine | 1.0% w/w |
| Dimethylguanidine | 4.5% w/w |
| Alkyl (C8-18) polysaccharide surfactant | 2.5% w/w |
| Sodium lactate | 3.5% w/w |
| Trilithium nitrilotriacetate | 0.75% w/w |

EXAMPLE 3

| | |
|---|---|
| Pure water | 72.55% w/w |
| Alkyl (C8-14) tributyl phosphonium iodide | 7.0% w/w |
| BromoCide 30 5% gel (Biolabs Inc.)[1] | 1.9% w/w |
| Alkyl (C7-18) polyethylene oxide (5-12 ETO) | 3.5% w/w |
| N-methyl cysteine | 2.3% w/w |
| Monoethanolamine | 4.5% w/w |
| Lithium ethylenediaminetetraacetate | 0.75% w/w |
| Hexyleneglycol | 7.5% w/w |

[1] 35% w/w 1-bromo-3chloro-5,5 dimethyl hydantoin

EXAMPLE 4

| | |
|---|---|
| Pure water | 15.0% w/w |
| Gemini surfactant [2] | 6.5% w/w |
| Bromine water, 15% [3] | 8.5% w/w |
| Dodecyl amine oxide | 2.0% w/w |
| Alkyl (C8-18) polysaccharide | 0.5% w/w |
| Lithium citrate | 0.65% w/w |
| Monoethanolamine sulphamate | 2.5% w/w |
| Dipropylene glycol | 64.35% w/w |

[2] 7,11-didecyl 3,6,9, 12, 15, pentaoxo-heptanone-1,17-di(trimethyl ammonium) chloride
[3] PCT 3026 Liquid Bromide Biocide. ProChemTech International Inc., USA.

EXAMPLE 5

Two Part System

| Part A | |
|---|---|
| Potassium sesquisilicate ($K_3SiO_3$) | 3.0% w/w |
| Potassium Tetra pyrophosphate | 2.0% w/w |
| Dipotassium EDTA[4] | 0.75% w/w |
| Lithium glyxolate | 0.5% w/w |
| Benzalkonium chloride | 3.0% w/w |
| Alkyl (c8-18) tributyl phophonium chloride | 3.5% w/w |
| N-methyl pyrrolidone | 7.5% w/w |
| Dipropyleneglycol methylether | 7.5% w/w |
| Demineralised water | 72.25% w/w |

[4] ethylenediaminetetraacetate

| Part B | |
| --- | --- |
| Alkyl (C8-18) tributyl phophonium chloride | 14.5% w/w |
| Bromocide 30 (Biolabs Inc.) | 4.75% w/w |
| Triethylene glycol | 35.0% w/w |
| Demineralised water | 45.75% w/w |

The above formulations may each have a pH within the range 4 to 12 at use dilution. Each formulation can be diluted from 1 part plus 4 parts water to 1 part to 250 parts of water, the water being soft in composition. Under normal endoscopic reprocessing procedures a concentration of 1 to 5% by volume is indicated depending upon the procedure and the extent of soiling resulting from the particular procedure.

The invention claimed is:

1. A composition for the removal of biofilms from substrate surfaces comprising an aqueous solution of the reaction product of:
   (a) one or more quaternary halide surfactant, said one or more quaternary halide surfactant comprising one or more halide ion, with
   (b) a source of bromine ions, wherein the bromine ions react with the one or more halide ion of the quaternary halide surfactant, and wherein the bromine ions are present in the ratio of 1 halide ion forming part of the quaternary halide surfactant to 0.05 to 8 moles of bromine ions in said aqueous solution.

2. A composition according to claim 1 wherein the quaternary halide surfactant is a quaternary chloride or iodide surfactant.

3. A composition according to claim 1 wherein the source of bromine ions is derived from an inorganic source.

4. A composition according to claim 1 wherein the source of bromine ions is derived from an organic source.

5. A composition according to claim 1 wherein the quaternary halide surfactant is a mono or di-quaternary halide surfactant.

6. A composition according to claim 1 which additionally comprises one or more non-ionic or zwitterion surfactants.

7. A composition according to claim 1 which additionally comprises one or more phosphate esters or ethers dissolved in water, or mixtures of water and polar solvent selected from the group consisting of C(1-6) alcohols, ethers, esters and ketones.

8. A composition according to claim 1 which additionally comprises one or more ingredients selected from the group consisting of detergent additives, hydrotropes, inorganic and organic buffering agents, sequestering and chelating agents, viscosity control additives, dyes and perfumes compatible with the other ingredients.

9. A composition according to claim 1 wherein the one or more quaternary halide surfactants has one halide ion, and the pH is in the range 4 to 12 at in-use dilution.

10. A composition according to claim 9 which additionally comprises one or more non-ionic or zwitterion containing surfactants.

11. A composition according to claim 9 wherein the quaternary halide surfactant is a quaternary chloride or iodide surfactant.

12. A composition according to claim 9 which additionally comprises:
   a) one or more phosphate esters: and/or
   b) one or more polar solvents partly or wholly soluble in water.

13. A composition according to claim 9 which additionally comprises one or more other common ingredients of commercial detergents selected from the group consisting of hydrotropes, inorganic and or organic buffering agents, sequestering or chelating agents, viscosity control additives, dyes and perfumes.

14. A composition according to claim 1 wherein:
   (a) the one or more quaternary halide surfactant is selected from an alkyl or alkyl aryl (C8-18) mono or di quaternary halide surfactant and said one or more halide ion is selected from chloride or iodide, and wherein said alkyl or alkyl aryl (C8-18) mono or di quaternary halide surfactant is present in an amount of from 1 part per million to 250,000 parts per million;
   (b) the source of bromine ions is an aqueous solution or other source containing from 0.1 to 200,000 parts per million of bromine ions; and wherein said composition additionally comprising:
   (c) one or more non-ionic or zwitterion containing surfactants comprising a hydrophobe containing 7 to 20 carbon atoms;
   (d) a mucolytic agent;
   (e) a phosphate ester or ether;
   (f) a low molecular weight nitrogen containing solvent having a molecular weight of less than 120;
   (g) one or more polar alcohol, glycol, ester, ether or ketone solvents having a molecular weight of less than 200;
   (h) and optionally one or more hydrotropic agents, inorganic or organic buffering agents, and other common detergent additives;
   and the pH of said composition is from 4 to 12.

15. A composition according to claim 1 formulated as a dilutable concentrated product or as a diluted ready to use product provided in the form of: a) a single package containing all ingredients; b) two or more packages containing one or more of the ingredients of the formulation.

* * * * *

UNITED STATES PATENT AND TRADEMARK OFFICE
CERTIFICATE OF CORRECTION

| | | |
|---|---|---|
| PATENT NO. | : 8,012,461 B2 | |
| APPLICATION NO. | : 11/629052 | |
| DATED | : September 6, 2011 | |
| INVENTOR(S) | : Whiteley et al. | |

It is certified that error appears in the above-identified patent and that said Letters Patent is hereby corrected as shown below:

On title page, Item (73) should be deleted and Item (73) should be inserted as attached
    -- Whiteley Corporation Pty Ltd, North Sydney (AU) --

Signed and Sealed this
Twenty-seventh Day of March, 2012

David J. Kappos
*Director of the United States Patent and Trademark Office*

(12) United States Patent
Whiteley et al.

(10) Patent No.: US 8,012,461 B2
(45) Date of Patent: Sep. 6, 2011

(54) BIOFILM REMOVER

(75) Inventors: Reginald Keith Whiteley, North Manly (AU); Marilyn Emily Karaman, Waratah West (AU)

(73) Assignee: Whiteley Corporation Pty Ltd, North Sydney (AU)

( * ) Notice: Subject to any disclaimer, the term of this patent is extended or adjusted under 35 U.S.C. 154(b) by 842 days.

(21) Appl. No.: 11/629,052

(22) PCT Filed: Jun. 1, 2005

(86) PCT No.: PCT/AU2005/000782
§ 371 (c)(1),
(2), (4) Date: Feb. 19, 2007

(87) PCT Pub. No.: WO2005/120592
PCT Pub. Date: Dec. 22, 2005

(65) Prior Publication Data
US 2008/0317877 A1    Dec. 25, 2008

(30) Foreign Application Priority Data
Jun. 8, 2004  (AU) .............................. 2004903116

(51) Int. Cl.
*A61L 9/00* (2006.01)
*C11D 1/62* (2006.01)
(52) U.S. Cl. .................................... 424/70.28; 422/28
(58) Field of Classification Search .............. 422/28; 424/70.28
See application file for complete search history.

(56) References Cited

U.S. PATENT DOCUMENTS

| | | | |
|---|---|---|---|
| 4,978,685 A | * | 12/1990 | Gannon et al. ............. 514/642 |
| 2003/0161758 A1 | * | 8/2003 | Whiteley .................... 422/28 |

* cited by examiner

*Primary Examiner* — Sean E Conley
(74) *Attorney, Agent, or Firm* — Pryor Cashman LLP; Andrew S. Langsam, Esq.

(57) ABSTRACT

A composition for the removal of biofilms from substrate surfaces formed by reacting: (a) one or more quaternary halide surfactants with (b) a source of reactive bromine ions in the ratio of 1 halide ion forming part of the quaternary surfactant to 0.05 to 8 moles of bromine ions in aqueous solution.

15 Claims, No Drawings